US005702553A

United States Patent [19]

Iskra et al.

[11] Patent Number: 5,702,553
[45] Date of Patent: Dec. 30, 1997

[54] METHOD OF FORMING A PAPERBOARD TAMPON APPLICATOR HAVING AN OUTWARDLY ROLLED GRIPPER END

[75] Inventors: Michael J. Iskra, Bridgewater; Martin Wislinski, Edison, both of N.J.

[73] Assignee: McNeil-PPC, Inc., Milltown, N.J.

[21] Appl. No.: 742,332

[22] Filed: Nov. 1, 1996

Related U.S. Application Data

[63] Continuation of Ser. No. 366,536, Dec. 30, 1994, abandoned.

[51] Int. Cl.⁶ .................... B29C 53/56; B29C 57/04
[52] U.S. Cl. .................... 156/203; 264/310; 264/322; 264/339; 264/340; 264/345; 493/297; 493/299; 493/303
[58] Field of Search .................... 264/68, 310, 322, 264/339, 340, 345; 156/203; 493/297, 299, 303

[56] References Cited

U.S. PATENT DOCUMENTS

| | | |
|---|---|---|
| 2,509,241 | 5/1950 | Mende . |
| 3,433,225 | 3/1969 | Voss et al. . |
| 3,633,469 | 1/1972 | Kinney . |
| 4,106,396 | 8/1978 | Richards et al. . |
| 4,375,969 | 3/1983 | Woerz .................... 493/158 |
| 4,412,833 | 11/1983 | Wiegner et al. .................... 604/14 |
| 4,508,531 | 4/1985 | Whitehead .................... 604/14 |
| 4,573,964 | 3/1986 | Huffman .................... 604/15 |
| 4,726,805 | 2/1988 | Sanders, III .................... 604/15 |
| 4,755,164 | 7/1988 | Hinzmann .................... 493/288 |
| 5,087,239 | 2/1992 | Beastall et al. .................... 604/14 |
| 5,290,501 | 3/1994 | Klesius .................... 264/322 |
| 5,346,468 | 9/1994 | Campion et al. .................... 604/13 |
| 5,614,230 | 3/1997 | Weyenberg et al. .................... 264/310 X |

FOREIGN PATENT DOCUMENTS

| | | |
|---|---|---|
| 581 136 | 2/1994 | European Pat. Off. . |
| 626 254 | 11/1994 | European Pat. Off. . |
| 186674 | 9/1936 | Switzerland . |

OTHER PUBLICATIONS

Derwent DIALOG® WPI Acc No: 96–333732/33, WO96/20682 (published Jul. 11, 1996).

*Primary Examiner*—Leo B. Tentoni

[57] ABSTRACT

A method of forming an improved finger grip at the gripper end of a paperboard tampon tube is disclosed. This gripper end has an outwardly rolled edge produced by applying moisture to the gripper end of the paperboard tube having a diameter of less than about 25 mm, heating a forming tool to about 100° F. to about 350° F., rotating the paperboard tube with respect to the forming tool at a rate of about 50 to 1000 rpm, and contacting the gripper end of the paperboard tube with the forming tool for about 0.2 to about 5 seconds. In this manner, the forming tool rolls the gripper end of the paperboard tube outwardly to form a radiused surface at the outside of the gripper end of the paperboard applicator tube. The resulting tampon applicator is also disclosed.

12 Claims, 5 Drawing Sheets

METHOD OF FORMING A PAPERBOARD TAMPON APPLICATOR HAVING AN OUTWARDLY ROLLED GRIPPER END

This is a continuation of application Ser. No. 08/366,536, filed Dec. 30, 1994, now abandoned.

FIELD OF THE INVENTION

This invention relates to a method of fabricating paperboard tampon applicators having a diameter of less than about 25 mm which have an outwardly rolled finger grip.

BACKGROUND OF THE INVENTION

Paperboard tampon applicators which include a pair of telescoping cylinders are well known in the art. For example, Wiegner et al., U.S. Pat. No. 4,412,833; Beastall et al., U.S. Pat. No. 5,087,239; Hinzmann, U.S. Pat. No. 4,755,164; Huffman, U.S. Pat. No. 4,573,964; Whitehead, U.S. Pat. No. 4,508,531; all teach various aspects of these applicators.

Tampon applicators, whether paperboard or plastic, generally incorporate surface features at the rear or gripper end to allow the user to more or less securely hold the applicator while ejecting the tampon from the opposite end of the applicator. While plastic applicators can generally have pronounced gripper ends by nature of their fabrication, the gripper end configuration of paperboard applicators is more limited. For example, Wiegner et al. teaches a lightly grooved grip; Beastall et al., teaches a series of more pronounced grooves forming rings in the gripper end; Hinzmann discloses both a grip area having a reduced diameter and surface indentations; and Whitehead and Huffman both teach finger grip areas having substantially reduced diameter. Each of the finger grips taught in this prior art has a limited ability to prevent finger slip during ejection of the tampon.

Paperboard applicators have been limited by the of deformation accepted by the paperboard applicator stock before it is destroyed by the grip-forming process steps. Therefore, the finger grip areas are generally only formed with minimal raised rings or grooves.

In view of the shortcomings of the prior art, what is needed is a paperboard tampon applicator which has increased distortion of the tampon applicator stock to provide for more pronounced finger grips.

SUMMARY OF THE INVENTION

The present invention relates to a method of forming an improved finger grip at the gripper end of a tampon tube. This gripper end has an outwardly rolled edge produced by applying moisture to the gripper end of the paperboard tube having a diameter of less than about 25 mm, heating a forming tool to about 100° F. to about 350° F., rotating the paperboard tube with respect to the forming tool, preferably at a rate of about 10 to 1000 rpm, and contacting the gripper end of the paperboard tube with the forming tool for about 0.2 to about 5 seconds. In this manner, the forming tool rolls the gripper end of the paperboard tube outwardly to form a radiused surface at the outside of the gripper end of the paperboard applicator tube.

The present invention works well with paperboard tampon tubes which are formed either by the spiral winding of paper and/or cardboard layers to form a continuous tube or by the rolling of relatively rectangular, paperboard tube blanks. The more pronounced finger grip allows the use of slicker coatings on the applicator tube surface.

DETAILED DESCRIPTION OF THE INVENTION

Figure 1:
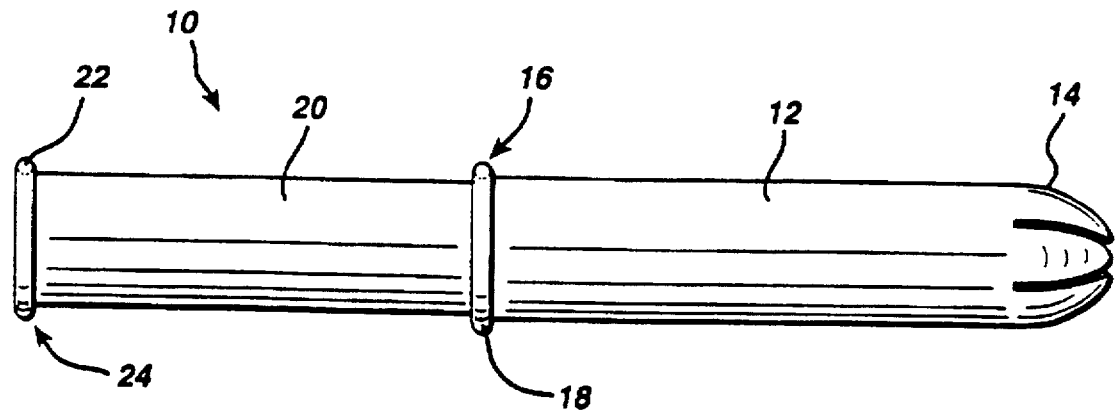
FIG. 1 illustrates a paperboard tampon applicator having outwardly rolled gripper ends.
Figure 2:
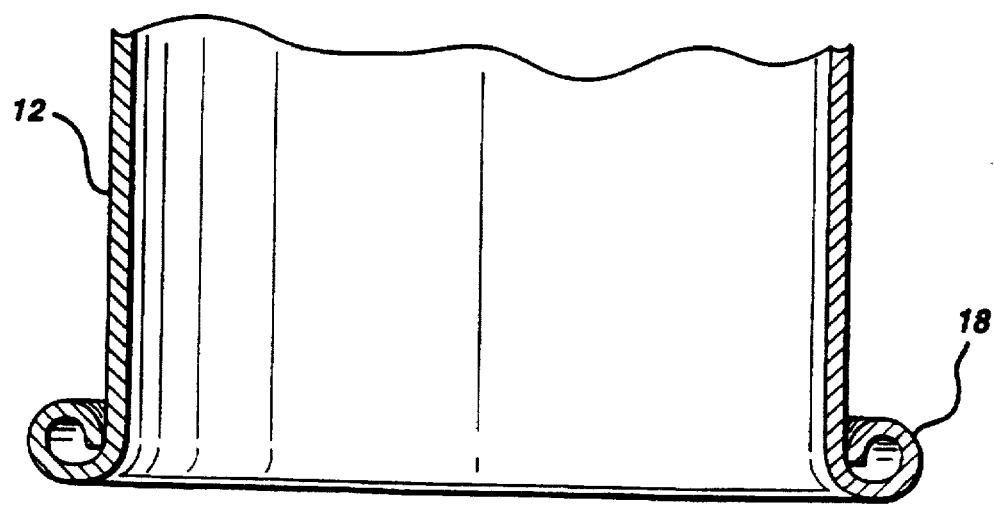
FIG. 2 illustrates an enlarged cross-section along line 2—2 of FIG. 1.
Figure 3:
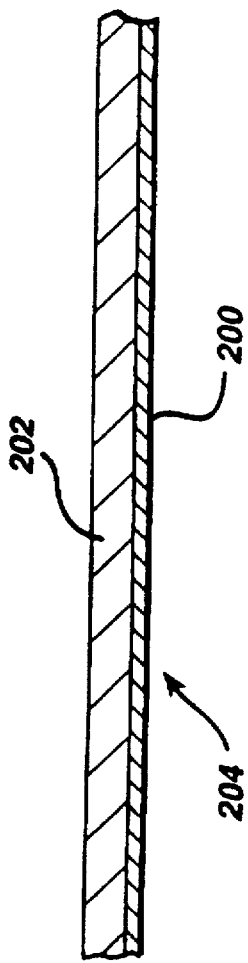
FIG. 3 illustrates an enlarged cross-section of the laminated tube stock which is used in a preferred embodiment.
Figure 4:
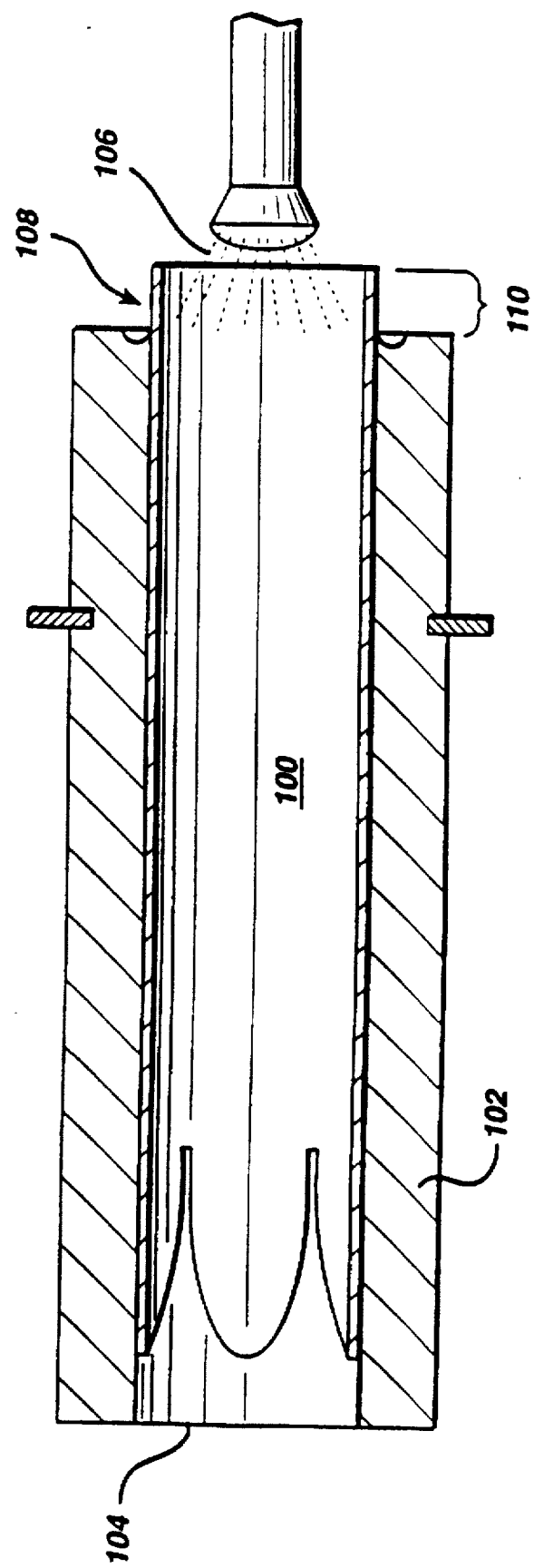
FIG. 4 illustrates the moistening of the gripper end of a tube in preparation for the edge rolling process.

Referring initially to FIGS. 1 and 2, the tampon applicator 10 includes at least one tube 12 having an ejection end 14 and a gripper end 16. The tube 12 has an outwardly rolled edge 18 at its gripper end 16. In use, the barrel 12 of a tampon applicator 10 is generally held between a user's thumb and middle finger, while the plunger 20 is manipulated by the user's index finger. The rolled edge 18 forms a flange at the end of the barrel 12 which helps to keep it from slipping through the user's finger as the plunger 20 is pushed into the barrel 12. Of course, the plunger 20 may also be formed of a paperboard tube and may include an outwardly rolled edge 22 at its gripper end 24.

Referring now to FIGS. 4 and 5A–5C, a previously formed tube 100 having a diameter of less than about 25 mm is seated in a collet device 102 which holds the tube 100 firmly in place while also providing a stop 104 to allow the correct seating depth. The collet 102 holding the tube 100 is then rotated to provide for at least one rotation of the tube 100 during the formation of the outwardly rolled edge. Thus, if it takes about one second to form a rolled edge from tube-to-forming tool contact until the edge is fully rolled, without any additional dwell time, the collet device 102 would rotate at a speed of at least about 60 rpm. Under preferred applicator forming conditions, the collet device 102 would rotate at a speed of about 10 rpm to about 1,000 rpm, more preferably, about 50 rpm to 500 rpm, and most preferably about 100 rpm to 380 rpm.

Moisture 106 is applied to the tube 100 in the region of the gripper end 108 to help to soften the fibers in the rolling zone 110 to reduce material splitting. The moisture 106 is preferably applied after the collet 102 is rotated, but moisture 106 may also be applied before the tube 10 is rotating on the collet 102. Moisture 106 can be applied as a fine mist of water, steam, water spray, dipping into an aqueous bath, and the like. It is preferred that about 5 to 50 mg of moisture is added to the tube 100 at the gripper end 108 to facilitate the edge rolling procedure. More preferably, about 10 to 30 mg, and most preferably, about 10 to 20 mg of moisture is added to the tube 100.

Figure 5A:
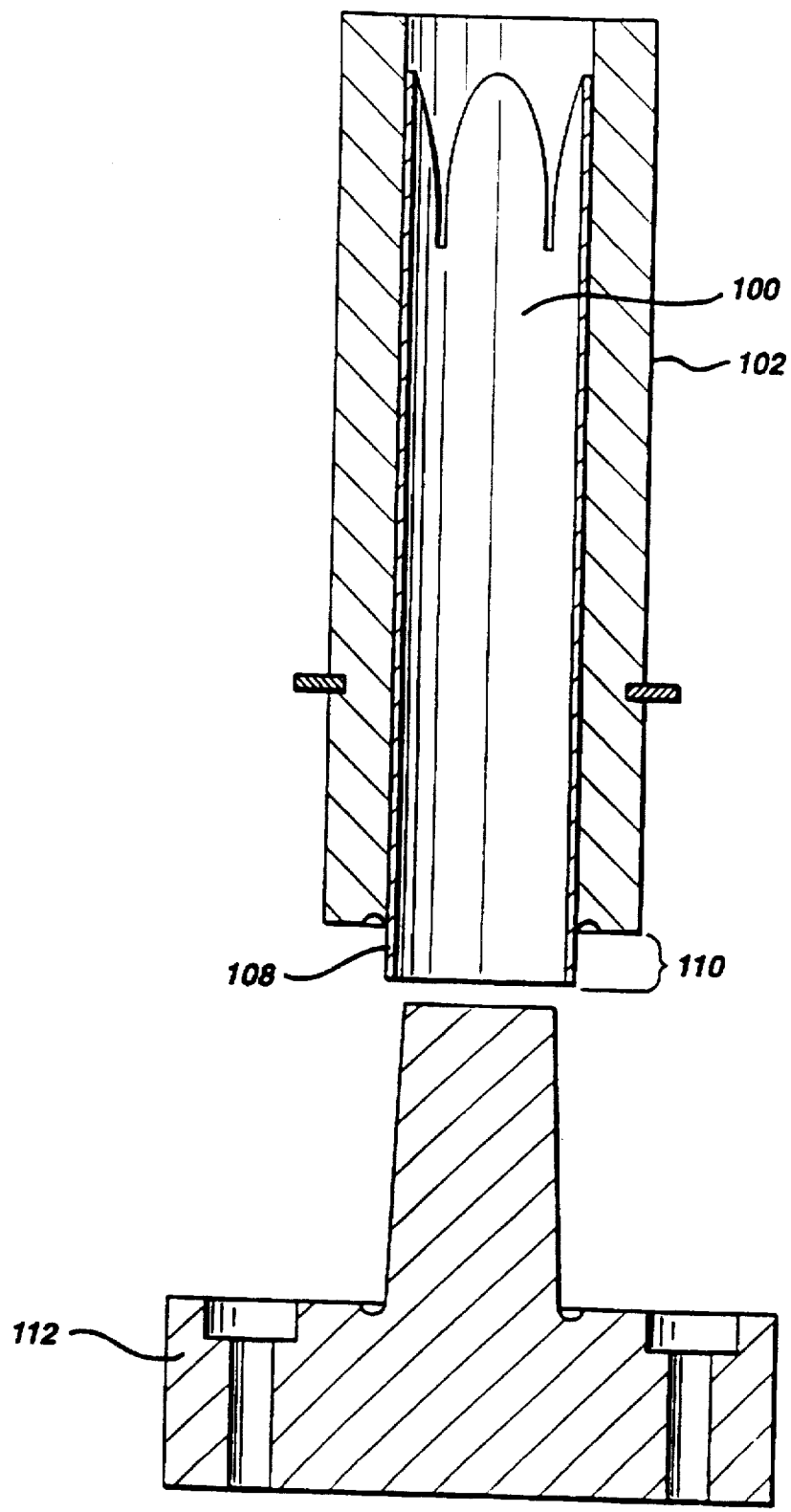
FIGS. 5A–5C depict the sequence of forming the outwardly rolled edge in a tampon applicator barrel.
Figure 5B:
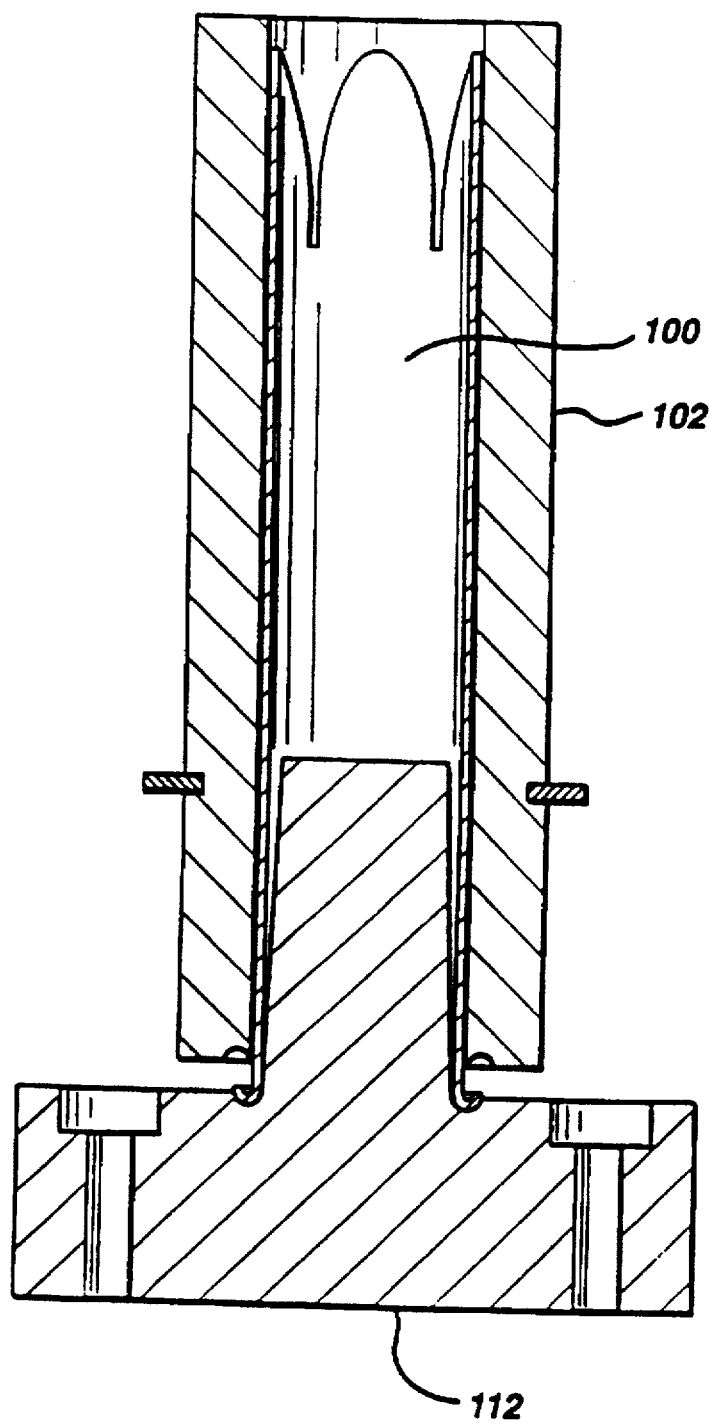
Figure 5C:
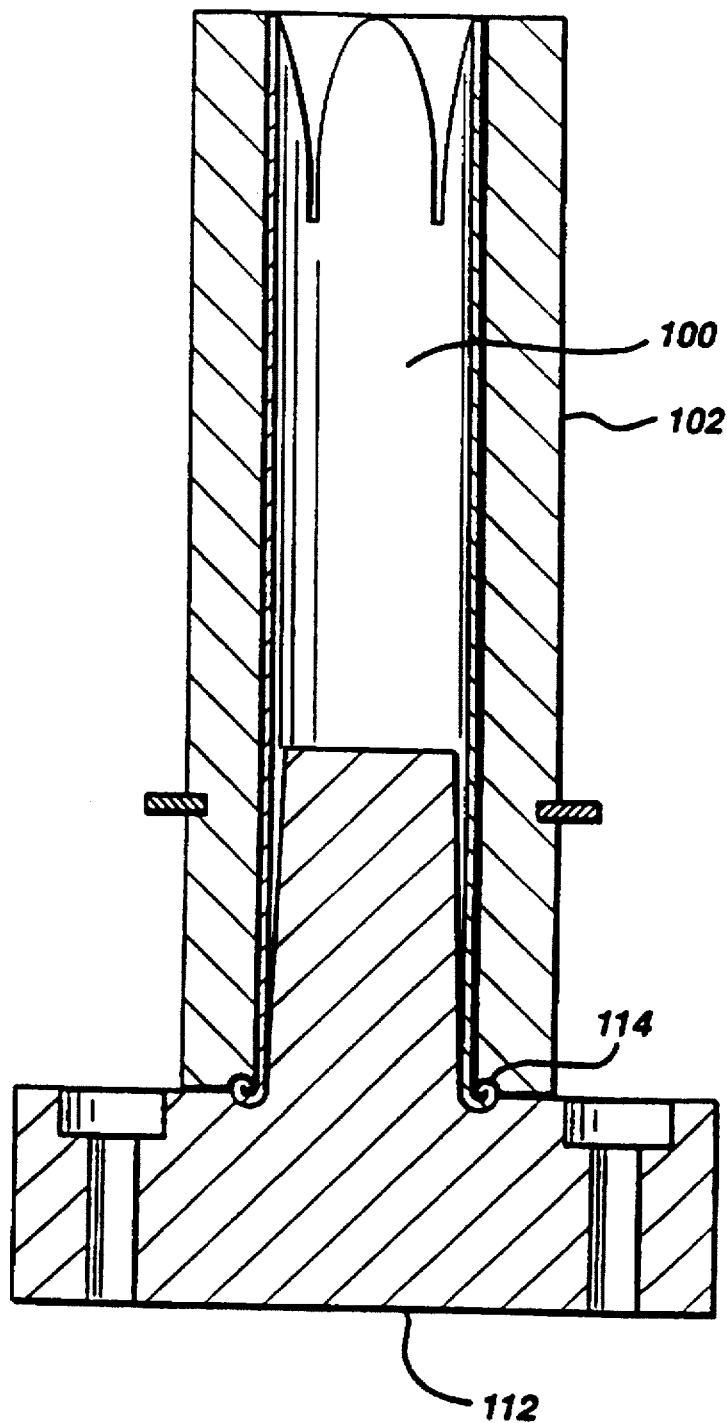

The moistened tube 100 which is rotating in the collet device 102 is then brought into contact with a stationary forming tool 112 (FIGS. 5A–5C). Preferably, the collet device 102 is moved toward the forming tool 112 at about 2.5 cm/sec to about 11.5 cm/sec. In a particularly preferred embodiment, the collet device 102 is moved toward the forming tool 112 at about 6 cm/sec. The forming tool 112 may be heated to about 100° F. to about 350° F., preferably about 200° F. to 250° F., and more preferably about 225° F. After the tube 100 contacts the forming tool 112 (FIG. 5B), the collet device 102 continues to move toward the forming tool 112, thereby feeding a sufficient length of the rolling zone 110 of the tube 100 into the forming tool 112 to roll the gripper edge 108 of the tube 100 outwardly to form a finger grip flange 114. The exact amount of tube 100 which is fed into the forming tool 112 will generally depend on the radius of the rolled edge 114, which will be recognized by the ordinarily skilled practitioner. When the collet device 102 reaches its maximum extension toward the forming tool 112 (FIG. 5C), it may be held for about 0.25 to about 5 seconds to set the rolled shape 114.

After the desired forming time has been reached, the collet device 102 is retracted from the forming tool 112 and the finished tube 100 is ejected from the collet 102. While the invention is herein described with reference to a stationary forming tool 112 and rotating, moving collet device 102 holding the tube 100, the invention also functions with other combinations as long as the relative rotation and movement between the tube 100 and forming tool 112 are maintained. The resulting rolled edge 114 can have a radius of about 0.5 to 2 mm, preferably about 0.75 to about 1.25 mm, and most preferably, about 1 mm.

The heat of friction caused by rotating the tube 100 with respect to the forming tool 112 along with the applied heat tend to drive off the applied moisture 106 in the rolling process. In addition, the heating step also stabilizes the rolled shape 114. Finally, it is helpful to drive off all applied moisture 106 in order to reduce the likelihood of the applicator tube fostering the growth of undesirable microorganisms. Such growth can be detrimental to the health of the user of the tampon applicator.

The forming tool 112 preferably has a low friction surface where the tube edge 108 is rolled. This surface can be a highly polished surface, such as stainless steel, a teflon-coated surface, and preferably, a teflon-coated stainless steel surface. Additional lubrication provided, e.g., by wax and other known lubricants can also improve the edge rolling process.

In a particularly preferred embodiment, a cardboard barrel and plunger are fabricated by laminating a waxed paper layer 200 to a cardboard layer 202 to provide applicator stock 204 having a thickness of about 0.3 to 0.4 mm. The barrel and plunger may then be formed into a tube having wax outer surface and a longitudinal seam, as described, for example in EP-A-0 581 136, or U.S. Pat. No. 4,755,164, the disclosures of which are herein incorporated by reference. Of course, this invention may also be used with spiral-wound tubes. The barrel and plunger tubes which are formed have an inside diameter of about 14.5 mm and 13 mm, respectively. Generally, the plunger will have a smaller diameter than the barrel in order to be accommodated within the barrel. We have found that we can form outwardly rolled edges on tubes having an inside diameter of less than about 25 mm, preferably about 10 to 20 mm, and most preferably, about 11 to 18 mm. The gripper ends of both the barrel and plunger tubes may then be rolled according to the present invention to result in the tampon applicator illustrated in FIG. 1 wherein a tampon pledget is enclosed in the barrel.

The useful paperboard stock for the formation of the applicator tubes will be recognized by the skilled artisan. A representative, non-limiting list of such stock includes paperboard, cardboard, cup stock, paper, and the like. The stock can have a thickness of about 0.2 to 0.5 mm. This stock may be laminated or coated with a cover layer to provide a smoother outer surface to the tampon applicator tube. The cover layer may have a thickness of about 0.01 to 0.1 mm. A representative, non-limiting list of such cover layer material includes wax, plastic, and the like. A representative, non-limiting list of plastic material includes polyolefins such as polyethylene and polypropylene, polyesters such as polyethylene terephthalate, cellophanes, nitrocelluloses, and the like.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of forming an outwardly rolled edge on a gripper end of a paperboard tampon applicator tube, the method comprising the steps of:

applying moisture to the gripper end of the paperboard tube having a diameter of less than about 25 mm;

heating a forming tool to about 100° F. to about 350° F.;

rotating the paperboard tube with respect to the forming tool in order to provide at least one rotation of the tube during the formation of the outwardly rolled edge;

contacting the gripper end of the paperboard tube with the forming tool for about 0.2 to about 5 seconds to form the outwardly rolled edge; whereby the forming tool rolls the gripper end of the paperboard tube outwardly to form a radiused surface at the outside of the gripper end of the paperboard applicator tube.

2. The method of claim 1 wherein the step of applying moisture to the gripper end of the paperboard tube comprises applying a spray of an aqueous solution.

3. The method of claim 1 wherein the step of applying moisture to the gripper end of the paperboard tube comprises applying steam.

4. The method of claim 1 wherein the paperboard tube is rotated with a collet.

5. The method of claim 1 wherein the rolled edge has a radius of less than about 2 mm.

6. The method of claim 5 wherein the rolled edge has a radius of about 1 mm.

7. The method of claim 1 comprising heating the forming tool to about 200° F. to about 250° F.

8. The method of claim 1 comprising rotating the paperboard tube with respect to the forming tool at about 10 rpm to about 1,000 rpm.

9. The method of claim 8 comprising rotating the paperboard tube with respect to the forming tool at about 100 rpm to about 380 rpm.

10. The method of claim 4 wherein the step of contacting the gripper end of the paperboard tube with the forming tool comprises advancing the rotating collet toward the forming tool at a rate of about 2.5 cm/sec to about 11.5 cm/sec.

11. The method of claim 1 further comprising forming a paperboard tube by spirally winding a plurality of plies of a continuous paper stock.

12. The method of claim 1 further comprising forming a paperboard tube by rolling a substantially rectangular blank and joining together opposite blank edges to form a seam.

* * * * *